United States Patent [19]

Dahan

[11] Patent Number: 5,078,742
[45] Date of Patent: Jan. 7, 1992

[54] POSTERIOR CHAMBER LENS IMPLANT

[76] Inventor: Elie Dahan, 84 Troon Road, Greenside, Johannesburg, Transvaal, South Africa

[21] Appl. No.: 529,411

[22] Filed: May 29, 1990

[30] Foreign Application Priority Data

Aug. 28, 1989 [ZA] South Africa .................. 89/6547

[51] Int. Cl.$^5$ ............................................. A61F 2/16
[52] U.S. Cl. ...................................................... 623/6
[58] Field of Search .............................................. 623/6

[56] References Cited

U.S. PATENT DOCUMENTS

| 4,476,591 | 10/1984 | Arnott | 623/6 |
| 4,585,456 | 4/1986 | Blackmore | 623/6 |
| 4,664,666 | 5/1987 | Barrett | 623/6 |
| 4,673,406 | 6/1987 | Schlegel | 623/6 |
| 4,701,181 | 10/1987 | Arnott | 623/6 |

FOREIGN PATENT DOCUMENTS 0106448  9/1983  European Pat. Off.
84/6570  8/1984  South Africa.

*Primary Examiner*—Ronald Frinks
*Attorney, Agent, or Firm*—Lowe, Price, Leblanc & Becker

[57] ABSTRACT

A posterior chamber lens implant 10 formed of a soft material comprises a lens 12, a pair of flexible and resilient holding arms 14, 16 formed integrally with and projecting from the periphery of the lens 12 and lying in substantially the same plane as the lens 12, each arm 14, 16 having a first end 22 formed integrally with the lens 12 and a second end 24 distanced from the periphery of the lens 12, and a flexible web 18, 20 associated with each arm 14, 16 each web 18, 20 stretching between and being formed integrally with the periphery of the lens 12 and the second end 24 of its associated arm 14, 16. The webs 18, 20 are designed to hold the arms 14, 16 in position to prevent them flopping about during implantation and use of the lens implant 10. However, the webs 18, 20 are formed of a flexible material and thus it is possible to compress the arms 14, 16 towards the periphery of the lens 12 to assist in insertion of the lens implant 10 into the capsular bag or the ciliary sulcus of the eye.

5 Claims, 1 Drawing Sheet

U.S. Patent  Jan. 7, 1992  5,078,742
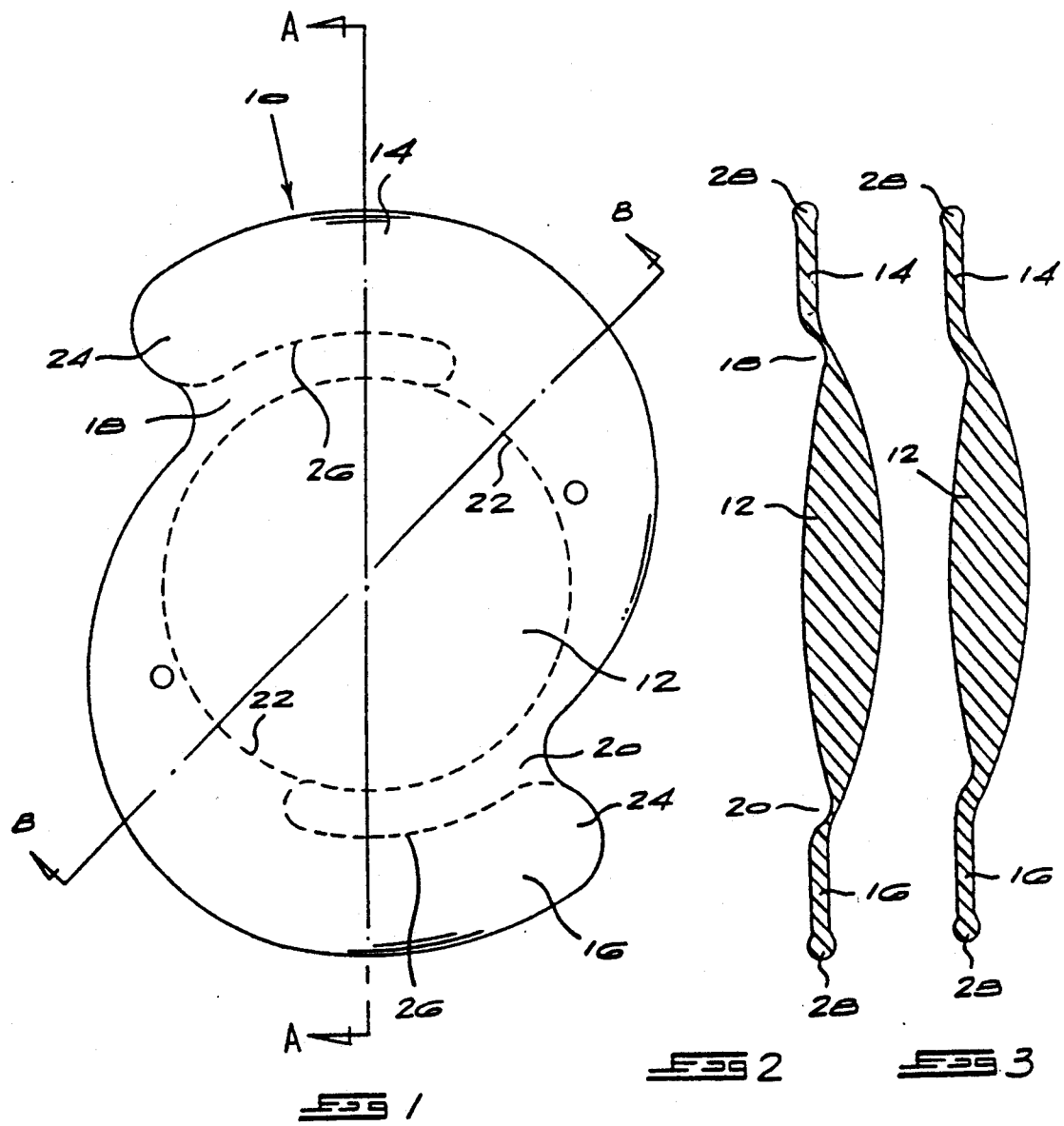

POSTERIOR CHAMBER LENS IMPLANT

BACKGROUND OF THE INVENTION

This invention relates to a posterior chamber lens implant which is made of a soft material.

Posterior chamber lens implants which comprise an optical part or lens and two or more holding arms or loops or flanges are known. For example, these lens implants are disclosed and described in European Patent Specification No. 0106488, U.S. Pat. Nos. 4,476,591 and 4,701,181. The arms function to hold the lens implant in place in the capsular bag or the posterior chamber between the posterior capsule and the iris, after the lens implant has been inserted in the eye.

These lens implants are usually made of polymethylmethacrylate (PMMA) which is a hard material which imparts sufficient rigidity to the arms to prevent them from flopping or buckling during or after implantation.

Hydrophilic and silicone rubber materials are however softer and more flexible and do not possess sufficient rigidity to prevent the arms of a lens implant made from such a material from flopping or buckling during use. Thus, to date, lens implants made from a soft material have been provided not with holding arms, but with two opposed flaps for holding the lens implant in place in the eye. For example, these lens implants are disclosed and described in South African Patent No. 84/6570. These flaps do not however provide the same advantages as arms or loops, because forces applied to the flaps are transmitted to the optical part of the lens causing buckling of the lens.

There is thus a need for a new design of lens implant made from a soft material.

SUMMARY OF THE INVENTION

According to the invention there is provided a posterior chamber lens implant formed of a soft material which comprises a lens; a pair of opposed flexible and resilient holding arms formed integrally with and projecting from the periphery of the lens and lying in substantially the same plane as or in a plane substantially parallel to the plane of the lens, each arm having a first end formed integrally with the lens and a second end distanced from the periphery of the lens; and a flexible web associated with each arm, each web stretching between and being formed integrally with the periphery of the lens and the second end of its associated arm.

By a "soft" material there is meant a hydrophilic material or a silicone rubber material or the like.

The two arms preferably lie in a flat plane which is the plane containing the periphery of the lens or a plane parallel thereto, but they may alternatively be in planes which are inclined to this plane by a small angle of up to 10° and it is this that is meant by saying that the arms be substantially in the plane of the lens or in a plane substantially parallel thereto.

Preferably, each web stretches between the periphery of the lens and the inner edge of its associated arm to fill the entire region between the periphery of the lens and the inner edge of its associated arm.

Preferably, the arms are C-shaped.

Preferably, the cross-sectional thickness of the web is substantially less than the cross-sectional thickness of the arms. For example, the arms preferably have a thickness of about 0.3 mm while the webs may have a thickness of about 0.1 mm.

Preferably, the arms include peripheral reinforcement, for example, a rib, arranged along and formed integrally with the outer edge of each arm. The ribs preferably have a thickness of about 0.4 mm.

DESCRIPTION OF THE DRAWINGS

FIG. 1 is a schematic front view of a posterior chamber lens implant of the invention;

FIG. 2 is a sectional side view along the line A—A of the lens implant of FIG. 1; and FIG. 3 is a sectional side view along the line B—B of the lens implant of FIG. 1.

DESCRIPTION OF EMBODIMENTS

Referring to the drawings there is shown a posterior chamber lens implant 10 consisting of a lens 12, two C-shaped arms 14, 16 and two webs 18, 20. Each arm 14, 16 has a first end 22 attached to and formed integrally with the periphery of the lens 12 and a second end 24 distanced from the periphery of the lens 12. Flexible webs 18, 20 stretch between the periphery of the lens 12 and the inner edges 26 of the arms 14, 16, thus filling the region between the periphery of the lens 12 and the inner edges 26 of the arms 14, 16. The two arms 14, 16 lie in a plane substantially parallel to the plane of the lens 12. It can be seen that the two arms 14, 16 follow a step-vaulted line which is first 10° to 20° inclined to the plane of the lens 12 and then is parallel to the plane of the lens 12.

Each arm 14, 16 includes a rib 28 at its outer edge for reinforcing purposes and to prevent buckling.

Referring to FIG. 2, it can be seen that the cross-sectional thickness of the arms 14, 16 is substantially greater than the cross-sectional thickness of the webs 18, 20.

The lens 12, the arms 14, 16 and the webs 18, 20 are all formed integrally with one another from a suitable soft material such as HEMA 38% water, which is a hydrophilic material, or a silicone rubber.

The webs 18, 20 are designed firstly to hold the arms 14, 16 in position to prevent them flopping about during implantation and use of the lens implant 10. However, the webs 18, 20 are formed of a flexible material and thus it is still possible to compress the arms 14, 16 towards the periphery of the lens 12 to assist in insertion of the lens implant 10 into the capsular bag or the ciliary sulcus of the eye. When the lens implant 10 is in place in the capsular bag or the ciliary slucus, the arms, 14, 16, being resilient, spring outwardly again to hold the lens implant 10 in place in the capsular bag or the ciliary sulcus.

I claim:

1. A posterior chamber lens implant formed of a soft material which comprises:
   a lens;
   a pair of opposed flexible and resilient holding arms formed integrally with and projecting from the periphery of the lens and lying in substantially the same plane as or in a plane substantially parallel to the plane of the lens, each arm having a first end formed integrally with the lens and a second end distanced from the periphery of the lens, each arm including a reinforcing rib arranged along and formed integrally with the outer edge of each arm; and
   a flexible web associated with each arm, each web stretching between and being formed integrally with the periphery of the lens and the second end of its associated arm to fill the entire region between the periphery of the lens and the inner edge of its associated arm, each arm having a thickness of about 0.3 mm, each web having a thickness of about 0.1 mm and each rib having a thickness of about 0.4 mm.

2. A lens implant according to claim 1 wherein the arms are C-shaped.

3. A lens implant according to claim 1 wherein the soft material is a hydrophilic material.

4. A lens implant according to claim 3 wherein the soft material is HEMA 38% water.

5. A lens implant according claim 1 wherein the soft material is a silicone rubber.

* * * * *